United States Patent
Liu et al.

(12) United States Patent (10) Patent No.: US 11,413,374 B2
(45) Date of Patent: Aug. 16, 2022

(54) OSTEOCHONDRAL SCAFFOLD

(71) Applicant: UCL Business LTD, London (GB)

(72) Inventors: Chaozong Liu, London (GB); Gordon Blunn, London (GB)

(73) Assignee: UCL BUSINESS LTD, London (GB)

( * ) Notice: Subject to any disclaimer, the term of this patent is extended or adjusted under 35 U.S.C. 154(b) by 53 days.

(21) Appl. No.: 16/068,540

(22) PCT Filed: Jan. 9, 2017

(86) PCT No.: PCT/GB2017/050033
§ 371 (c)(1),
(2) Date: Oct. 17, 2018

(87) PCT Pub. No.: WO2017/118863
PCT Pub. Date: Jul. 13, 2017

(65) Prior Publication Data
US 2019/0009004 A1    Jan. 10, 2019

(30) Foreign Application Priority Data
Jan. 8, 2016 (GB) ..................................... 1600385

(51) Int. Cl.
| | | |
|---|---|---|
| *A61L 27/36* | (2006.01) |
| *A61L 27/06* | (2006.01) |
| *A61L 27/24* | (2006.01) |
| *A61L 27/12* | (2006.01) |
| *A61L 27/56* | (2006.01) |
| *A61F 2/30*  | (2006.01) |
| *A61L 27/58* | (2006.01) |
| *A61L 27/18* | (2006.01) |
| *A61L 27/22* | (2006.01) |

(52) U.S. Cl.
CPC .............. *A61L 27/365* (2013.01); *A61F 2/30* (2013.01); *A61L 27/06* (2013.01); *A61L 27/12* (2013.01); *A61L 27/18* (2013.01); *A61L 27/24* (2013.01); *A61L 27/3654* (2013.01); *A61L 27/56* (2013.01); *A61L 27/58* (2013.01); *A61F 2002/30214* (2013.01); *A61L 27/222* (2013.01); *A61L 27/225* (2013.01); *A61L 27/227* (2013.01); *A61L 2430/02* (2013.01); *A61L 2430/06* (2013.01); *A61L 2430/24* (2013.01)

(58) Field of Classification Search
None
See application file for complete search history.

(56) References Cited

U.S. PATENT DOCUMENTS

| | | | |
|---|---|---|---|
| 6,013,853 A | 1/2000 | Athanasiou et al. | |
| 9,155,543 B2 * | 10/2015 | Walsh | A61F 2/30756 |
| 9,724,203 B2 * | 8/2017 | Nebosky | A61F 2/44 |
| 2005/0043814 A1 | 2/2005 | Kusanagi et al. | |
| 2008/0262616 A1 * | 10/2008 | McKay | A61L 27/48 |
| | | | 623/14.12 |
| 2014/0012393 A1 | 1/2014 | Shin et al. | |
| 2014/0324169 A1 | 10/2014 | Maher et al. | |

FOREIGN PATENT DOCUMENTS

| | | | |
|---|---|---|---|
| EP | 1277450 A2 | | 1/2003 |
| EP | 1948089 A1 | * | 7/2008 |
| EP | 2450066 | * | 10/2010 |
| EP | 2450066 A1 | | 5/2012 |
| JP | 2003180814 A | | 7/2003 |
| WO | 2005/047467 A2 | | 5/2005 |
| WO | WO 2014/041416 | * | 3/2014 |

OTHER PUBLICATIONS

Zhao et al. "Preparation of porous PLGA/Ti biphasic scaffold and osteochondral defect repair" 2013.*
Haaparanta et al. "Preparation and characterization of collagen/PLA, chitosan PLA, and collagen/chitosan/PLA hybrid scaffolds for tissue engineering" 2013.*
Li et al. "Bone ingrowth in porous titanium implants produce by 3D fiber deposition"2007.*
Of Kikuchi "Hydroxyapatite/Collagen Bone-like Nanocomposite"2013/.*
United Kingdom Intellectual Property Office, Search Report issued in corresponding Application No. GB 1600385.7, dated Jun. 24, 2016.
European Patent Office, International Search Report issued in corresponding Application No. PCT/GB2017/050033, dated Apr. 10, 2017.

* cited by examiner

*Primary Examiner* — Danah Al-Awadi
(74) *Attorney, Agent, or Firm* — Stites & Harbison, PLLC; Terry L. Wright (57) ABSTRACT

There is described a multiphasic osteochondral scaffold for osteochondral defect repair, the scaffold comprising a bone phase and a cartilage phase, wherein the bone phase comprises a support matrix and the cartilage phase comprises a polymeric matrix, and the scaffold comprises a non-porous layer between the bone phase and the cartilage phase. Also described is a multiphasic osteochondral scaffold for osteochondral defect repair, the scaffold comprising a bone phase and a cartilage phase, wherein the bone phase comprises a support matrix and the cartilage phase comprises a polymeric matrix, and wherein the support matrix is tapered so that the dimensions of the support matrix are less at the lower end of the support matrix than at the upper end of the support matrix.

21 Claims, 8 Drawing Sheets

(a) The joint level is restored (b) poor fill in control group

FIG. 10

OSTEOCHONDRAL SCAFFOLD

FIELD OF THE INVENTION

The invention relates to an osteochondral scaffold, a method of producing an osteochondral scaffold and its use in orthopaedic therapy. The scaffold is a functionally biomimetic osteochondral scaffold which can be used for cartilage and osteochondral defect (OCD) repair.

BACKGROUND TO THE INVENTION

Osteoarthritis (OA) is a degenerative joint disease (Litwic, A., et al. (2013). British Medical Bulletin 105: 185-199). Individuals with OA often experience joint pain and reduced joint function unless appropriate treatment is adopted. It affects over 18% of the population when they reach their mid-50s. This figure rises to over 52% by the time they reach their mid-70s. More than 650,000 people in the UK have painful OA in one or both hips, and more than 6 million people have OA in one or both knees. It may start slowly with mild to moderate symptoms; pain typically may occur on motion or after inactivity.

Cartilage transplantation has been explored as a treatment option for cartilage defects. Autologous Osteochondral Transfer (OATS) for example allows reconstruction with functional hyaline cartilage tissue, ideally with congruent sliding surfaces. However, donor site morbidity, limited availability of matching donor tissues, a high complication rate as well as early degenerative changes of the transplanted cartilage are well-known disadvantages. The excessive bone formation caused by the healing leads to subchondral stiffening which leads to the degeneration of the overlying cartilage. Nosewicz et al. (Nosewicz T L, Reilingh M L, van Dijk C N, Duda G N, Schell H. Knee surgery, sports traumatology, arthroscopy: official journal of the ESSKA. 2012; 20:1923-30) analysed the healing of those donor sites in an in vivo sheep model and found an irregular and incomplete restoration of the subchondral bone plate, native and reparative cartilage degeneration, collapse of the sclerotic subchondral bone and cartilage, an increase in the primary defect through osseous erosion and the formation of a central cavitary lesion.

The current state of the art in terms of surgical intervention of osteoarthritis is a joint replacement operation. This will happen when the loss of quality of cartilage and bone at the joint interface has significantly reduced the quality of life of the patient, and non-surgical treatments are no longer effective. These are major surgical procedures, which are only undertaken when the disease has progressed to the stage where there is no alternative but a severely limited lifestyle. This can mean that patients will have suffered long periods of pain, discomfort and reduced mobility before an operation is performed. Joint replacement has been thought of as one of the most significant medical device innovations. However, implants do not come without risk or complications. A growing number of implant recipients have experienced implant failure and other severe complications associated with their joint replacements. Therefore, the early repair of cartilage and/or osteochondral defects to stop or delay joint replacement has a significant impact on public healthcare (Baker, C. L. and C. M. Ferguson (2005). Orthopedics 28(2): S227-S234).

The treatment of cartilage and osteochondral defects remains a challenge because treatments to date have failed to achieve a complete restoration of the joint cartilage surface and its properties. Many new technologies, such as osteochondral tissue engineering and stem cell therapies, have been studied and applied to the repair of osteochondral defects (Nesic, D., et al. (2006). Advanced Drug Delivery Reviews 58(2): 300-322). The goal of a tissue engineering approach is to repair the cartilage and osteochondral defect in the joint and restore its function in order to delay or remove the need for a joint replacement.

Treatments using tissue engineering methods have been established and are promising for the treatment of small cartilage defects. In this approach, 3D scaffolds (with or without cells) have been used to provide support for tissue growth. Commercially available osteochondral scaffolds have been used for the treatment of these small cartilage and osteochondral defects (<1.5 $cm^2$). However, none of these products promotes satisfactory durable regeneration of large cartilage and osteochondral defects.

The main issues for current commercially available osteochondral defect treatments are poor cartilage fill and associated fibrocartilaginous repair rather than hyaline cartilage, as well as poor osteochondral repair (Christensen, B. B., et al. (2015); Knee Surgery, Sports Traumatology, Arthroscopy: 1-8). It is believed that this is due to weak biomechanical properties and lack of hydrostatic pressure that have been shown to enhance chondrocytes growth. This results in an inappropriate physical environment for cartilage healing.

SUMMARY OF THE INVENTION

The osteochondral scaffold of the invention is thought to provide an appropriate physical environment (that includes the generation of an appropriate biomechanical environment and hydrostatic pressure) to support cartilage healing that is critical for cartilage fill and hyaline cartilage formation. This functional biomimetic osteochondral scaffold bridges the gap between small osteochondral defect treatment and joint replacement. It is hoped that it will provide clinicians with a viable treatment option in situations where the disease has progressed beyond a small defect, but where a full joint replacement could still be avoided. This would lead to tangible and clinically relevant results in a one-step surgical procedure for the treatment of large cartilage and osteochondral defects, relieving pain and improving quality of life by keeping people active.

In accordance with a first aspect of the invention, there is provided a multiphasic osteochondral scaffold for osteochondral defect repair, the scaffold comprising a bone phase and a cartilage phase, wherein the bone phase comprises a support matrix and the cartilage phase comprises a polymeric matrix, and the scaffold comprises a non-porous layer between the bone phase and the cartilage phase.

One advantage of the non-porous layer between the bone phase and the cartilage phase is that it acts as a barrier to prevent synovial fluid from diffusing into the subchondral bone (i.e. the bone phase) from the cartilage phase when subject to dynamic compressive load. This helps to build hydrostatic pressure within the cartilage layer which is a critical factor for chondrogenesis and helps to improve hyaline cartilage formation rather than fibrocartilage formation.

The bone phase of the scaffold comprises a support matrix. This support matrix allows osteogenesis of subchondral bone. Further, this support matrix provides mechanical support and stability to the overlaying cartilage and biological fixation once implanted into the osteochondral defect.

This helps to increase the cartilage fill, promoting hyaline cartilage formation, and reducing the formation of associated fibrocartilage.

The support matrix of the bone phase may be formed of any suitable material which provides an appropriate level of mechanical support to the cartilage phase and allows osteogenesis. Suitable materials include metals, ceramics and minerals. Suitable metals include titanium, stainless steel, tantalum and their alloys. Suitable ceramics and minerals include bioactive glass, calcium phosphates (e.g. beta-tricalcium phosphate (TCP), hydroxyapatite, biphasic calcium phosphate, etc.), calcium deficient apatite and combinations thereof. In some embodiments, the support matrix is formed of metal. Preferably, the support matrix is formed of titanium.

The support matrix is preferably porous. This allows infiltration of the matrix by cells, such as osteoblasts and osteocytes, in the process of osteogenesis. It also allows bone formation within the matrix. The unit cell size of the pores in the porous support matrix is preferably between about 0.1 mm and about 3 mm. In some embodiments, the unit cell size of the pores is between about 0.3 mm and about 2.5 mm. In other embodiments, the unit cell size of the pores is between about 0.5 mm and about 2.5 mm. In further embodiments, the unit cell size of the pores is between about 0.5 mm and about 2 mm. In particular embodiments, the unit cell size of the pores is between about 0.75 mm and about 2 mm. In various embodiments, the unit cell size of the pores is between about 0.75 mm and about 1.5 mm. In certain embodiments, the unit cell size of the pores is about 1 mm.

The porous support matrix should have a porosity which allows appropriate infiltration of cells and bone formation. The porosity of the porous support matrix is preferably between about 30% and 80%. In various embodiments, the porosity is between about 30% and 70%. In some embodiments, the porosity is between about 40% and 70%. In other embodiments, the porosity is between about 50% and 70%. In particular embodiments, the porosity is between about 50% and 60%.

In some embodiments, the support matrix can further comprise one or more additional components to modify the characteristics and/or properties of the support matrix. For example, in embodiments in which the support matrix is formed of metal (such as titanium, titanium alloy or tantalum) or ceramic (such as bioactive glass), the support matrix may further comprise one or more calcium phosphate such as beta-tricalcium phosphate, hydroxyapatite and/or biphasic calcium phosphate. This helps to promote bone regeneration. In preferred embodiments, the support matrix further comprises hydroxyapatite.

In various embodiments, the support matrix may further comprise one or more polymers. For example, the support matrix may further comprise one or more polymer selected from collagen, poly(lactic-co-glycolic acid) (PLGA), polylactic acid (PLA), polycaprolactone (PCL), polyvinyl alcohol (PVA), polyvinyl pyrrolidone (PVP), polyethylene glycol (PEG), chitin, poly(hydroxyalkyl methacrylate), water-swellable N-vinyl lactams, starch graft copolymers, and derivatives and combinations thereof. In preferred embodiments, the support matrix further comprises collagen.

In particular embodiments, the support matrix further comprises a calcium phosphate (such as beta-tricalcium phosphate, hydroxyapatite and/or biphasic calcium phosphate) and a polymer such as collagen.

In various embodiments, the supporting structure of the support matrix is primarily formed from the main component from which it is formed, e.g. metal, ceramic and/or mineral. This provides a rigid backbone to the support matrix. The one or more additional components and/or the one or more polymers may be formed on this rigid backbone. For example, the rigid backbone of the support matrix can be formed first and then the one or more additional components and/or the one or more polymers can be caused to permeate or infiltrate into and/or through the rigid backbone.

The scaffold is intended to be used in the treatment of large cartilage and osteochondral defects. Therefore, the width and depth of the support matrix (when viewed in the orientation in FIG. 1) are between about 3 mm and about 20 mm, preferably between about 5 mm and about 15 mm, and more preferably between about 6 mm and about 10 mm. In some embodiments, the support matrix is broadly cylindrical and preferably has a diameter of between about 3 mm and about 15 mm, preferably between about 4 mm and about 10 mm. These dimensions are preferably the dimensions of the lower end of the support matrix, i.e. at the bottom end of the scaffold when viewed in the orientation in FIG. 1. The height of the support matrix may be between about 4 mm and about 12 mm, preferably between about 6 mm and about 10 mm.

Figure 1:
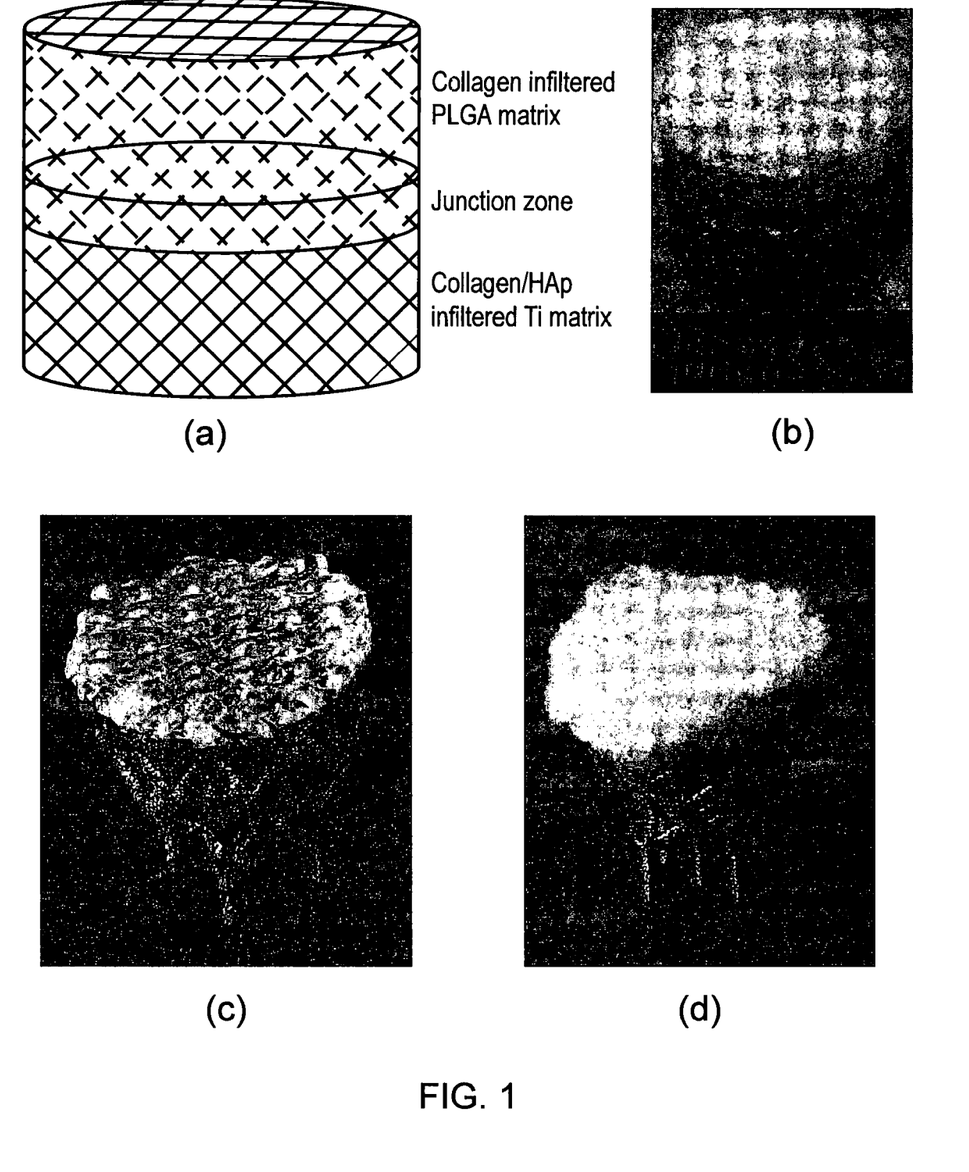

In preferred embodiments, the support matrix has a tapered profile so that the cross section of the support matrix at the lower end of the support matrix is less than the cross section of the support matrix at the upper end of the support matrix. Put another way, the dimensions (width and/or depth) of the support matrix at the lower end of the support matrix are less that the dimensions of the support matrix at the upper end of the support matrix. This tapered profile makes it easier to insert the scaffold into the osteochondral defect and reduces possible damage to host tissue. It also helps to ensure that once in situ, the scaffold is securely located in the osteochondral defect. The term "lower end of the support matrix" means the end of the support matrix which is situated furthest from the polymer matrix of the cartilage phase. In FIG. 1, this is the bottom end of the scaffold.

The term "upper end of the support matrix" means the end of the support matrix which is situated closest to the polymer matrix of the cartilage phase. In FIG. 1, this is the top end of the scaffold.

In some embodiments, the support matrix is tapered such that it is shaped as a truncated cone structure so that the lower end of the matrix has a smaller diameter than the upper end of the matrix (by the non-porous layer).

When the support matrix has a tapered profile, the angle of the taper is preferably between about 1° and about 45°. In some embodiments, the taper is between about 3° and about 30°. In other embodiments, the taper is between about 5° and about 30°. In various embodiments, the taper is between about 7° and about 20°. In particular embodiments, the taper is between about 10° and about 15°.

In some embodiments, the whole scaffold has a tapered profile. This means that the cross section of the scaffold at the lower end is less than the cross section of the scaffold at the upper end. Put another way, the dimensions (width and/or depth) of the scaffold at the lower end are less that the dimensions of the scaffold at the upper end. This tapered profile makes it easier to insert the scaffold into the osteochondral defect and also reduces possible damage to host tissue. It also helps to ensure that once in situ, the scaffold is securely located in the osteochondral defect.

The term "lower end of the scaffold" means the end of the scaffold formed by the support matrix. In FIG. 1, this is the bottom end of the scaffold.

The term "upper end of the scaffold" means the end of the support matrix which is formed by the polymeric matrix. In FIG. 1, this is the top end of the scaffold.

The scaffold may be tapered such that it is shaped as a truncated cone structure.

The angle of the taper of the scaffold is preferably between about 1° and about 45°. In some embodiments, the taper is between about 3° and about 30°. In other embodiments, the taper is between about 5° and about 30°. In various embodiments, the taper is between about 7° and about 20°. In particular embodiments, the taper is between about 10° and about 15°.

The cartilage phase of the scaffold comprises a polymeric matrix. This allows chondrogenesis in the cartilage layer within the osteochondral defect. Therefore, the polymeric matrix may be formed of any suitable polymer which allows chondrogenesis. The polymeric matrix of the cartilage phase may be formed of a natural or synthetic polymer. Suitable polymers include, but are not limited to, glycosaminoglycans (GAGs), GAG-like polysaccharides, collagen (type 1 & 2), gelatin, hyaluronic acid, fibrin, chitosan, chondroitin sulfate, poly(lactic-co-glycolic acid) (PLGA), polylactic acid (PLA), polycaprolactone (PCL), polyvinyl alcohol (PVA), tetraethylene glycol, chitin, starch graft copolymers, and derivatives and combinations thereof. In some embodiments, the polymeric matrix is formed of gelatin, hyaluronic acid, fibrin, chitosan, poly(lactic-co-glycolic acid) (PLGA), polylactic acid (PLA), polycaprolactone (PCL), polyvinyl alcohol (PVA), tetraethylene glycol, chitin, starch graft copolymers, or derivatives or combinations thereof. In preferred embodiments, the polymeric matrix is formed of poly(lactic-co-glycolic acid) (PLGA), polylactic acid (PLA), polycaprolactone (PCL) or combinations thereof.

In some embodiments, the polymeric matrix is formed of at least two polymers, for example, selected from the list of suitable polymers above. In particular embodiments, the first polymer may provide a supporting framework to the polymeric matrix and the second polymer can be formed on this supporting framework.

The first polymer, which can provide a supporting framework, may be selected from gelatin, hyaluronic acid, fibrin, chitosan, poly(lactic-co-glycolic acid) (PLGA), polylactic acid (PLA), polycaprolactone (PCL), polyvinyl alcohol (PVA), tetraethylene glycol, chitin, starch graft copolymers, and derivatives and combinations thereof. Preferably, the first polymer is selected from poly(lactic-co-glycolic acid) (PLGA), polylactic acid (PLA), polycaprolactone (PCL) or combinations thereof.

The second polymer, which can be formed on the supporting framework of the first polymer, may be selected from glycosaminoglycans (GAGs), GAG-like polysaccharides, collagen (type 1 & 2) and hyaluronic acid. Preferably, the second polymer is collagen (type 1 or 2).

In the embodiments described above, the supporting framework of the polymeric matrix can be formed of the first polymer and then the second polymer is permeated or infiltrated into and/or through the supporting framework.

The polymeric matrix is preferably porous. This allows infiltration of the matrix by cells, such as mesenchymal stem cells and chondrocytes, in the process of chondrogenesis. It also allows cartilage formation within the matrix. The unit cell size of the pores in the porous polymeric matrix is preferably between about 30 μm and about 500 μm. In some embodiments, the unit cell size of the pores is between about 40 μm and about 400 μm. In other embodiments, the unit cell size of the pores is between about 50 μm and about 300 μm. In further embodiments, the unit cell size of the pores is between about 60 μm and about 250 μm. In particular embodiments, the unit cell size of the pores is between about 70 μm and about 200 μm. In various embodiments, the unit cell size of the pores is between about 80 μm and about 150 μm. In certain embodiments, the unit cell size of the pores is between about 90 μm and about 120 μm.

The porous polymeric matrix should have a porosity which allows appropriate infiltration of cells and cartilage formation. The porosity of the porous polymeric matrix is preferably between about 30% and 90%. In some embodiments, the porosity is between about 40% and 80%. In other embodiments, the porosity is between about 50% and 80%. In particular embodiments, the porosity is between about 50% and 70%.

The scaffold is intended to be used in the treatment of large osteochondral defects. Therefore, the width and depth of the polymeric matrix (when viewed in the orientation in FIG. 1) are between about 5 mm and about 20 mm, preferably between about 6 mm and about 15 mm, and more preferably between about 6 mm and about 10 mm. In some embodiments, the polymeric matrix is generally cylindrical and preferably has a diameter of between about 4 mm and about 15 mm, preferably between about 5 mm and about 12 mm preferably between about 6 mm and about 10 mm. The height of the polymeric matrix may be between about 4 mm and about 8 mm.

As described above, the polymeric matrix may be tapered so that the entire scaffold is tapered.

The scaffold comprises a non-porous layer between the bone phase and the cartilage phase. This non-porous layer is in the region where the support matrix of the bone phase meets the polymeric matrix of the cartilage phase. Therefore, the non-porous layer can also be referred to as a junction layer. In some embodiments, the non-porous layer is between the support matrix and the polymeric matrix.

The term "non-porous" means that synovial fluid cannot move from the cartilage phase to the bone phase. This prevents synovial fluid from diffusing into the subchondral bone from the cartilage zone when subjected to compressive and torsional shear stresses, and this helps to build hydrostatic pressure within the cartilage and is a critical factor for chondrogenesis. For the avoidance of doubt, the term "non-porous" does not mean that the non-porous layer is impermeable to all molecules. Some small molecules may be able to pass through the layer. However, synovial fluid cannot. Therefore, put another way, the non-porous layer is impermeable to synovial fluid.

The non-porous layer may be formed from any suitable material which prevents the movement of synovial fluid into the bone phase. In some embodiments, the non-porous layer is formed from a polymer. In some embodiments, the non-porous layer is formed from the same polymer as the polymeric matrix. The non-porous layer may be formed of a natural or synthetic polymer. Suitable polymers include, but are not limited to, collagen, gelatin, hyaluronic acid, fibrin, chitosan, poly(lactic-co-glycolic acid) (PLGA), polylactic acid (PLA), polycaprolactone (PCL), polyvinyl alcohol (PVA), polyvinyl pyrrolidone (PVP), starch graft copolymers, and derivatives and combinations thereof. In some embodiments, the non-porous layer is formed of poly(lactic-co-glycolic acid) (PLGA), polylactic acid (PLA) or polycaprolactone (PCL) or combinations thereof.

In some embodiments, the non-porous layer acts to join the support matrix of the bone phase to the polymeric matrix of the cartilage phase. In particular embodiments, there is a partial overlap of the support matrix and the polymeric matrix and the non-porous layer is present in this region of overlap. For example, such an arrangement can be produced by partially melting one end of the polymeric matrix into the support matrix so that the melted polymer forms the non-porous layer in the top portion of the support matrix. This arrangement of having the polymeric matrix embedded in the support matrix provides the additional advantage of a strong join between the support matrix and polymeric matrix, i.e. between the bone phase and cartilage phase. This means that the scaffold provides good mechanical integration between layers to avoid delamination, and mechanical stability once implanted in the osteochondral defect.

The non-porous layer should be thick enough to withstand the hydrostatic pressure exerted on it once implanted. Preferably, the non-porous layer has a thickness of between about 0.5 mm and about 2 mm, and more preferably between about 0.5 mm and about 1.5 mm. In some embodiments, the non-porous layer has a thickness of about 1 mm.

The materials used to fabricate the scaffold should be biocompatible. This means that the materials do not elicit an immune response, foreign body reaction or cause any other adverse effect on the implant site or patient in general.

The scaffold is intended to mimic the naturally occurring osteochondral tissue structure and physical environment. In this way, it is a biomimetic.

The scaffold is a multi-layered osteochondral scaffold. In some embodiments, the scaffold is a tri-layered osteochondral scaffold. These three layers can be the support matrix, the polymeric matrix and the junction layer formed by the overlap between the support matrix and the polymeric matrix.

The scaffold may further comprise growth factors or drugs to promote tissue regeneration. For example, the polymeric matrix may comprise fibroblast growth factor (FGF), transforming growth factor beta (TGF-β), insulin-like growth factor (IGF) or vascular endothelial growth factor (VEGF). Further, the support matrix may comprise bone morphogenetic protein (BMP).

In some embodiments, the scaffold may comprise cells to promote tissue regeneration. For example, the polymeric matrix may further comprise chondrogenic cells or chondrocytes. "Chondrogenic cells" is meant to include any cell capable of chrondrogenic differentiation. In one embodiment, the scaffold is seeded with mesenchymal stem cells. In one embodiment, the mesenchymal stem cells are human mesenchymal stem cells. Examples of alternative cells for seeding include, but are not limited to, adipose derived stem cells, synovium derived stem cells, induced pluripotent stem cells, embryonic stem cells and fibrochondrocytes.

The scaffolds described above address the problems associated with current commercially available osteochondral scaffolds and are designed for the treatment of large osteochondral defect repairs. The scaffold is designed as a functionally gradient structure in terms of its structure, mechanical properties and functions. It features:

i. A strong subchondral bone section to provide strong support to the upper cartilage formation;
ii. A non-porous bone-cartilage junction section to link bone and cartilage sections, at the same time to maintain the hydrostatic pressure;
iii. A strong cartilage section for cartilage formation.

The advantages of this invention compared to alternatives lie in (1) it is stronger in its mechanical properties and can bear the necessary physical loads to achieve a stable mechanical fixation; (2) the non-porous interfacial zone between osseous and cartilaginous sections maintains hydrostatic pressure within the cartilaginous layer; (3) the strong bone integration provides support to formation, and enables cells within the cartilaginous layer to be subjected to a physiological dynamic environment.

Further, the scaffold of the present invention allows recruitment of cells from surrounding tissues including from the subchondral bone area. This provides improved tissue regeneration. In particular, the bone section enhances bone ingrowth into the matrix to form a strong integration with bone thus providing a stable mechanical support to the overlying cartilage, and which can bear the joint loading.

The osteochondral scaffold is a single unit, i.e. the bone phase and the cartilage phase (and the non-porous layer between the bone phase and the cartilage phase) are formed into a single unit which can be applied directly to an osteochondral defect. Therefore, it is not necessary to apply several different layers or sections during implantation of the scaffold. Further, no 'glue' is used during implantation to join the different layers. Such methods involving the use of multiple layers and glue are unable to prevent delamination of the top polymer from the bottom section when subjected to joint loading. However, the scaffolds of the present invention are a robust single unit which can withstand joint loading and remain intact.

The invention also provides a method of making a multiphasic osteochondral scaffold, the method comprising:
providing a support matrix;
providing a polymeric matrix; and
joining the support matrix to the polymeric matrix such that a non-porous layer is formed between the support matrix and the polymeric matrix.

The non-porous layer can be formed using a melt fusion method, for example, by ultrasound welding or by direct heating. A portion of the polymeric matrix can be partially melted and the portion of the polymeric matrix integrated into the support matrix. This partial melting and integration results in the formation of the non-porous layer within the uppermost part of the support matrix. This non-porous layer will have been formed from the polymer of the polymeric matrix.

The partial melting of a portion of the polymeric matrix can be achieved by heating the support matrix and moving (e.g. pressing) the polymeric matrix into the support matrix. Therefore, the heated support matrix melts the polymeric matrix so that it forms the non-porous layer. The polymeric matrix is preferably moved into the heated support matrix at between about 0.5 mm and about 2 mm per minute. Alternatively, the partial melting of a portion of the polymeric matrix can be achieved by an ultrasound welding method. The non-porous layer preferably has a thickness of between about 0.5 mm and about 2 mm.

The support matrix is heated to at least the melting point of the polymer. Preferably, the support matrix is heated to at least about 200° C., more preferably to at least about 250° C. Following melting of the polymeric matrix to form the non-porous layer, the scaffold is preferably cooled.

In accordance with another aspect of the invention, there is provided a multiphasic osteochondral scaffold for osteochondral defect repair, the scaffold comprising a bone phase and a cartilage phase, wherein the bone phase comprises a support matrix and the cartilage phase comprises a polymeric matrix, and wherein the support matrix is tapered so that the dimensions of the support matrix are less at the lower end than at the upper end of the support matrix.

Put another way, the cross section of the support matrix is less at the lower end than at the upper end of the support matrix. Alternatively, the dimensions of the cross section of the support matrix at the lower end are less that the dimensions of cross section at the upper end of the support matrix.

This tapered profile makes it easier to insert the scaffold into the osteochondral defect and also reduces possible damage to host tissue. Further, it helps to ensure that once in situ, the scaffold is securely located in the osteochondral defect.

In some embodiments, the support matrix is tapered such that it is shaped as a truncated cone structure so that the lower end of the matrix has a smaller diameter than the upper end of the matrix.

When the support matrix has a tapered profile, the angle of the taper is preferably between about 1° and about 45°. In some embodiments, the taper is between about 3° and about 30°. In other embodiments, the taper is between about 5° and about 30°. In various embodiments, the taper is between about 7° and about 20°. In particular embodiments, the taper is between about 10° and about 15°.

A skilled person will appreciate that the features described for the first aspect of the invention are equally applicable to this aspect of the invention. Therefore, the scaffold of this aspect of the invention can also have one, some or all of the features associated with the scaffold of the first aspect of the invention. For example, the scaffold may comprise a non-porous layer between the bone phase and the cartilage phase.

Also provided is a tapered osteochondral scaffold, wherein the dimensions of the scaffold are less at the lower end than at the upper end.

The features described above are also applicable to this aspect of the invention. Therefore, the scaffold may be tapered such that it is shaped as a truncated cone structure so that the lower end of the scaffold has a smaller diameter than the upper end of the scaffold.

The angle of taper of the scaffold is preferably between about 1° and about 45°. In some embodiments, the taper is between about 3° and about 30°. In other embodiments, the taper is between about 5° and about 30°. In various embodiments, the taper is between about 7° and about 20°. In particular embodiments, the taper is between about 10° and about 15°.

The invention also provides a method of making a multiphasic osteochondral scaffold, the method comprising:
  providing a support matrix;
  tapering the support matrix;
  providing a polymeric matrix; and
  joining the support matrix to the polymeric matrix to form the scaffold,
  wherein, after the scaffold has been formed, the dimensions of the support matrix are less at the lower end than at the upper end of the support matrix.

A skilled person will appreciate that the steps of the above method do not need to be carried out in the order given. For example, the support matrix and polymeric matrix can be provided and then joined to form the scaffold before the support matrix is tapered. Alternatively, the support matrix can be tapered before forming the scaffold.

The method may further comprise tapering the polymeric matrix. This will mean that the entire scaffold, once formed, is tapered.

Again, a skilled person will appreciate that the features described for the method of the first aspect of the invention are equally applicable to this method. For example, the support matrix may be joined to the polymeric matrix such that a non-porous layer is formed between the support matrix and the polymeric matrix. Further, this non-porous layer can be formed using a melt fusion method, for example, by direct heating or by an ultrasound fusion method.

Also provided is a tapered support matrix for use in the method described above. Various features of the tapered support matrix are described above.

Also provided is a tapered polymeric matrix for use in the method described above. Various features of the tapered polymeric matrix are described above.

The invention also provides the use of the scaffolds described above in osteochondral defect repair. For example, there is provided a method of treating an osteochondral defect, the method comprising implanting the scaffold described above into the osteochondral defect of a subject. Preferably the subject is a mammal such as a human.

BRIEF DESCRIPTION OF THE DRAWINGS

FIG. 1: (a) The schematic illustration of the titanium/PLGA framework reinforced collagen/hydroxyapatite composite osteochondral scaffold for large osteochondral defect repairs. The scaffold comprises of three sections: a hydroxyapatite/collagen filled titanium matrix base, a collagen infiltrated PLGA layer, and a junction that joins the titanium base with the PLGA/collagen layer. (b) Image of osteochondral scaffold showing the PLGA matrix joined to the titanium matrix, forming the framework of the osteochondral scaffold. The PLGA matrix is filled with collagen forming the cartilage layer. (c) Image showing a tapered titanium and PLGA scaffold. (d) Image showing a tapered titanium and collagen filled PLGA scaffold.

FIG. 7: Nano-Hydroxyapatite coated titanium scaffold (a), and Calcein AM staining indicated the cells grow happily on nano-hydroxyapatite coated titanium (b), and cells have higher proliferation than non-coated scaffold (c).

FIG. 9: Mechanical fixation of the scaffolds as determined by interfacial strength (a) and push-in and push-out strength (b).

FIG. 10: Three month post examination revealed that the cartilage defect levels were almost restored in the scaffold group (a); while poor fills were observed in the control group (b). The scores for scaffold group are significant higher than control group (c). The newly formed cartilage in scaffold group exhibited more resilient than that of control group (d).

DETAILED DESCRIPTION OF THE INVENTION

The invention will now be described in detail, by way of example only. This description is one specific way of carrying out the invention but is not to be considered limiting. The skilled person will appreciate that there are other ways of recreating the invention and these are also encompassed by the scope of the invention.

SUMMARY

The osteochondral scaffold is designed as a tri-layered truncated cone with conical tapered angle of 5-45°. It comprises a top collagen infiltrated PLGA layer, and a bottom collagen/hydroxyapatite infiltrated titanium layer. Alternatively, the bottom titanium layer may not be infiltrated. These two layers are joined to form a junction layer to mimic the tide mark in the osteochondral tissue. This osteochondral scaffold can achieve improved mechanical stability and biological fixation, improved cartilage fill and create hydrostatic pressure with the cartilage layer. It has the potential to lead to tangible and clinically relevant results in a one-step surgical procedure for treatment of large osteochondral defects. It is anticipated that this will create new treatments for early osteoarthritis.

The scaffold is based on a titanium and PLGA matrix reinforced collagen/hydroxyapatite "sandwich" composite system. The titanium and PLGA supporting framework are fabricated by a 3D rapid prototyping technique, and the porous framework will be filled with a collagen-hydroxyapatite composition which is spatially graded to form a structural and compositional scaffold. The composite scaffold is further treated using critical point-drying and cross-linking treatment. Then the scaffold is subjected to further surface processing in a plasma reactor to improve the cells attachment and ingrowth.

Fabrication of Scaffold

The osteochondral scaffold comprises a titanium matrix reinforced collagen/hydroxyapatite subchondral bone component, a PLGA matrix reinforced collagen layer as cartilage component, and a dense junction zone which joins the subchondral bone component and cartilage component together, as shown in FIG. 1. As mentioned above, the titanium matrix may not be infiltrated with collagen/hydroxyapatite.

Collagen type 1 is used to infiltrate the PLGA matrix and titanium matrix. Collagen dispersion (concentration from 0.5-2%) was prepared by adding the respective mass of collagen powder to 0.05M acetic acid solution (pH=3.2) and homogenizing on ice for 2 minutes, removing the air bubbles in a vacuum, and storing at 4° C. before use. To produce a collagen/hydroxyapatite dispersion, hydroxyapatite powder was dispersed under ultrasound sonication in 0.05M PVA solution at w/v concentration of 10%. The hydroxyapatite-PVA dispersion was then added to the collagen dispersion and homogenized on ice to produce a collagen-hydroxyapatite dispersion with a final collagen concentration of 1% and HA to collagen ratio of 70:30. The dispersion was de-gased in a vacuum and stored at 4° C. before use.

The titanium matrix was fabricated using a selective laser sintering (SLS) machine that uses a laser as the power source to sinter nano-titanium powder together to create a titanium matrix. The manufacturing process involves computer aided design of a titanium matrix which has a unit cell size of 0.5-2 mm, slicing the designed model and printing the matrix using a SLS machine. To increase the mechanical stability of the scaffold, the titanium matrix was designed and fabricated as a truncated cone structure with a taper angle of 5-45° such that the lower end of the matrix has a smaller diameter than the upper end of the matrix (to which the PLGA matrix is attached). The diameter of the lower end is in the range of 4-8 mm and the height in the range of 3-6 mm to adapt to different sizes of osteochondral defect.

The PLGA biopolymer matrix was fabricated by an indirect 3D printing technique using a 3D printer that runs on fused deposition modelling (FDM) technology by heating and extruding thermoplastic filament. In this process, a PVA negative mould was fabricated by FDM technology. PLGA in acetone solution (5-25% concentration) was cast in a PVA sacrificial negative mould. The acetone solvent was removed in a vacuum oven for 24 hours, and the PVA negative mould was dissolved away in running water. Then the matrix was critical point dried to obtain a dry PLGA matrix which has a unit cell size of 0.5-1.5 mm. The diameter of the lower end is in the range of 5-10 mm and the height in the range of 2-4 mm to adapt to different sizes of osteochondral defect. Apart from PLGA, PLA and PCL biopolymers could also be used in this application. The biopolymer matrix was subjected to 10 minutes UV processing in a UV/ozone reactor to improve its surface wettability.

The biopolymer matrix was joined to the titanium matrix by a partial melting fusion method. In this process, the titanium matrix was pre-heated to 250° C., then the biopolymer matrix was pressed 1 mm into the titanium matrix at a rate of 1 mm per minute by an Instron machine. The construct was then cooled in water to form a 1 mm strong junction layer between the titanium matrix and biopolymer matrix. The interfacial zone forms a dense layer to act as a barrier to prevent synovial fluid from diffusing into the subchondral bone when subject to compressive load, thus building hydrostatic pressure in the cartilage layer.

The PLGA component and titanium component of the obtained PLGA/titanium matrix was infiltrated with collagen solution and collagen/hydroxyapatite solution, respectively, under vacuum. The construct was frozen at −20° C. for 24 hours, followed by freeze drying to obtain an osteochondral scaffold that comprises a titanium matrix reinforced collagen/hydroxyapatite subchondral bone component, a PLGA matrix reinforced collagen layer as cartilage component, and a dense junction zone which joins the subchondral bone component and cartilage component together. A typical titanium/PLGA/collagen osteochondral scaffold with a unit cell of 1 mm is shown in FIG. 1.

The microstructure of the resultant scaffold was examined by scanning electron microscopy (SEM) (JEOL JSM-840F, JEOL). The pore size and size distribution of the samples were analysed by a high resolution micro X-ray computed tomography ($\mu$-CT) system ($\mu$CT 40, Scanco Medical, Switzerland) operated at a voltage of 55 kV and a current of 145 mA. A DualBeam™-SEM/FIB system (FEI Nova 600 Nanolab) fitted with an energy dispersive X-ray analysis (EDAX) (EDAX Genesis), which combines ultra-high resolution field emission SEM and precise Focused Ion Beam (FIB) etch and deposition, was used for interior microstructure examination and local elemental analysis, and for transmission electron microscopy (TEM) sample preparation. A TA ElectroForce® 3100 test instrument was used to analyse the mechanical property of the scaffold materials.

Sheep mesenchymal stem cells (hMSCs) were used for in vitro evaluation of the scaffold, and cellular behaviours were examined with respect to cells attachment, proliferation, and immunohistochemistry analysis.

Figure 2:
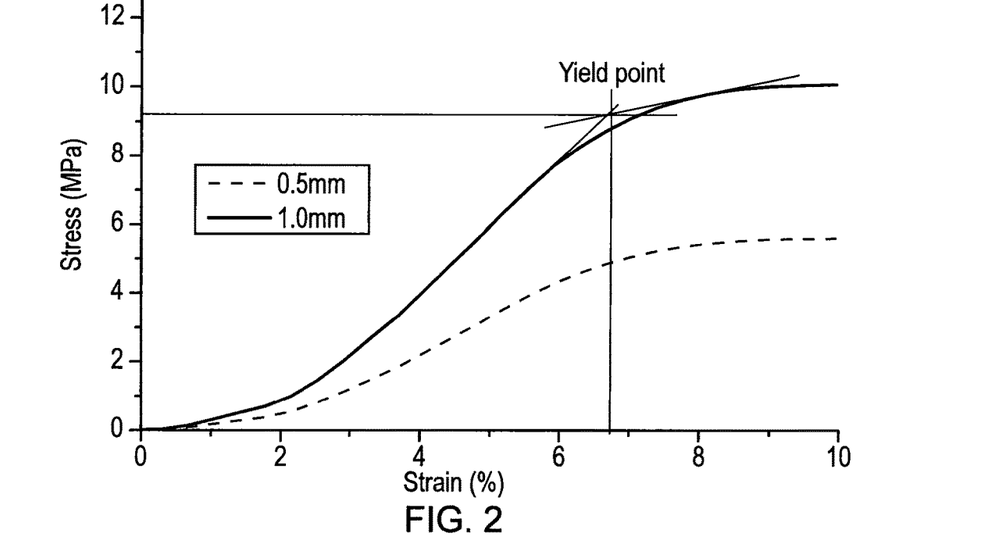
FIG. 2: An unconfined compressive test was performed on the cylindrical PLGA reinforcing collagen scaffold. Typical force-deformation curves show the scaffold deforms with compressive stress. After initial deformation, about 2% strain, the scaffold becomes stiffer. The scaffold yields at about 7% strain deformation. The yield strength for the scaffolds is in the range of 10-12 MPa, which is equivalent to or higher than that of the human knee articular cartilages.
Figure 3:
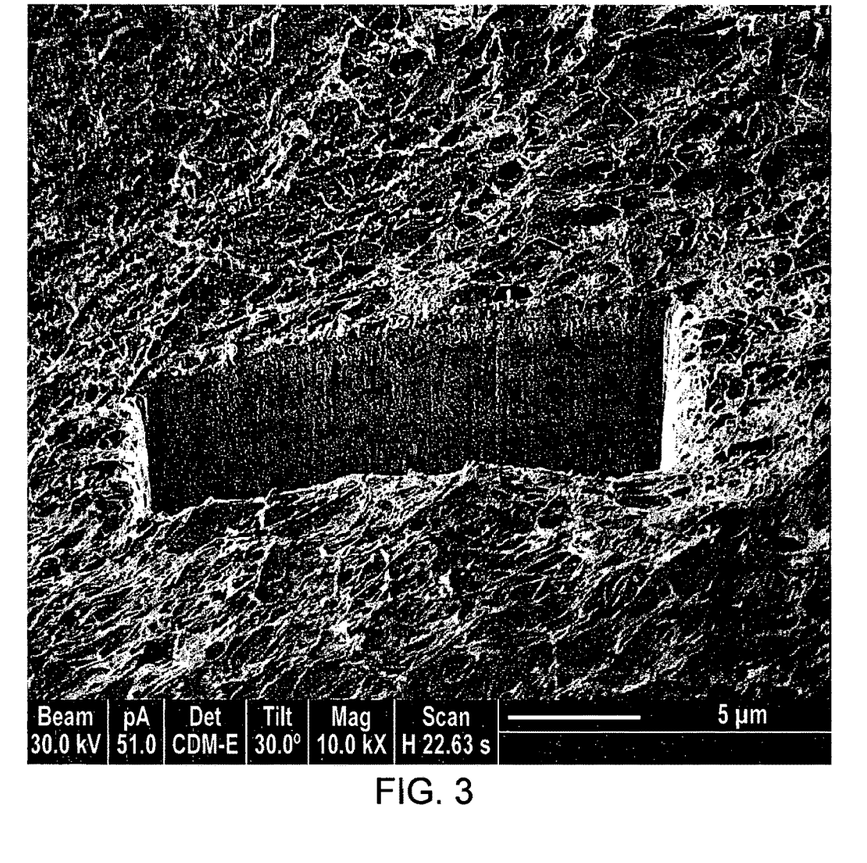
FIG. 3: Focused ion beam examination revealed the cells colonised the PLGA/Collagen composite and form a dense layer after two weeks of in vitro culture.
Figure 4:
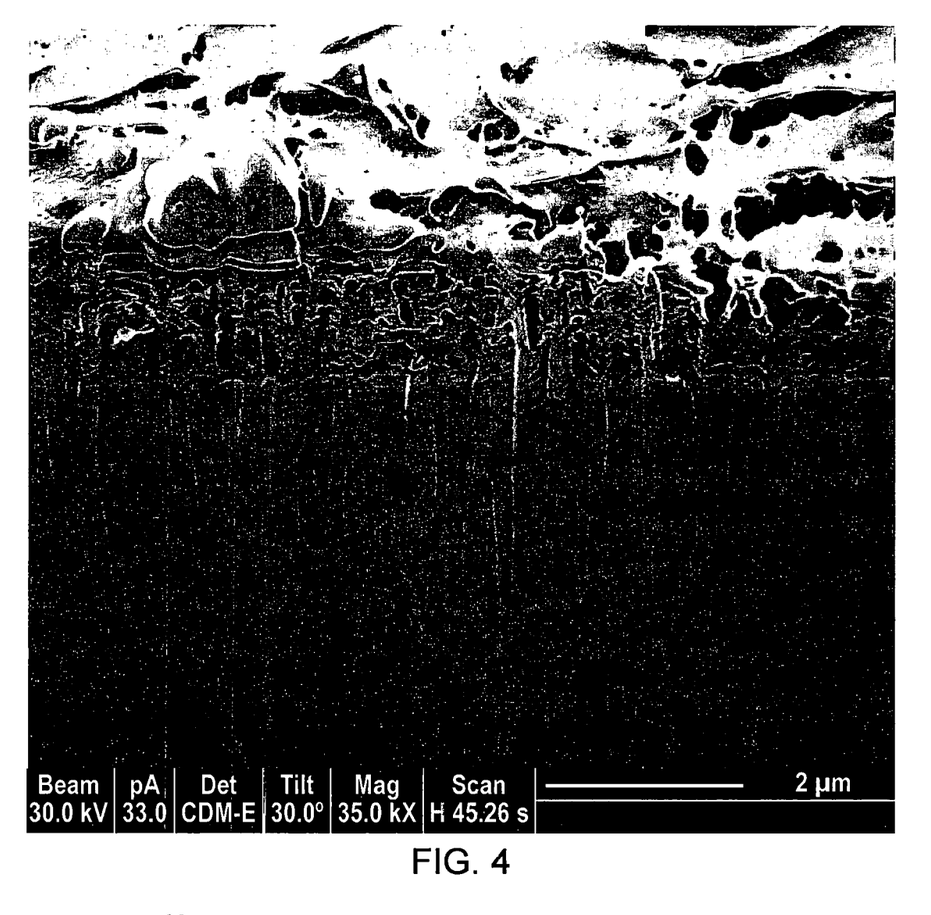
FIG. 4: Focused ion beam examination revealed that thin collagen/hydroxyapatite layer coated to the titanium, which support the cells growth. A dense cell layer formed after 2 weeks of in vitro culture.
Figure 5:
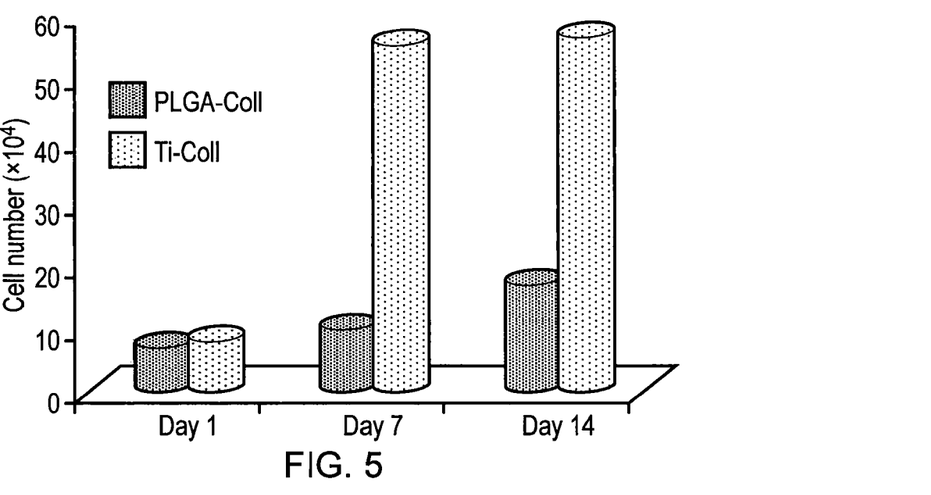
FIG. 5: Cell proliferation analysis (Alamar Blue Assay) demonstrated that cells colonise both the PLGA-collagen layer and the titanium-collagen-hydroxyapatite layer and proliferate there. A higher cell proliferation rate was identified in the titanium-collagen-hydroxyapatite layer than that in the PLGA-collagen layer.

The unconfined compressive test on cylindrical PLGA matrix reinforced collagen scaffold demonstrated that the scaffold has yield strength around 10 MPa, which is equivalent to or higher than that of the human knee articular cartilages, as shown in FIG. 2. In vitro evaluation of the scaffold using sheep mesenchymal stem cells (hMSCs) revealed that the cells were able to colonise the scaffolds, and the scaffolds can provide support for cells growth in both bone and cartilage sections of the osteochondral scaffold, as revealed by focused ion beam examination (FIGS. 3 & 4), and by cells proliferation analysis (FIG. 5).

Advantages of Scaffold

The inventors believe that the subchondral bone and adjacent cartilage form a functional unit, and that an appropriate stable physical environment provided by the osteochondral bone is crucial for the healthy growth of the overlying cartilage. The osteochondral scaffold combines components, namely a titanium matrix reinforced with collagen/hydroxyapatite (although the titanium matrix may not be infiltrated with collagen/hydroxyapatite) to direct formation of bone-like tissue at the distal region, and PLGA reinforced collagen for chondrogenesis in cartilage repair. The dense junction layer acts as "calcified cartilage" between articular cartilage and subchondral bone and forms a gradient structure with respect to mechanical properties, structure and composition.

The advantages provided by the scaffold lie in its structure design and associated functionality. This includes:

(1) The structural design of the osteochondral scaffold: the scaffold comprises a titanium matrix (either infiltrated with collagen/hydroxyapatite or without infiltration) subchondral bone component to provide an appropriate mechanical support to the overlaying cartilage, and a PLGA matrix reinforced collagen component for cartilage formation. It has the potential to improve mechanical stability and biological fixation once implanted into the osteochondral defect. This increases the cartilage fill, promoting hyaline cartilage formation, and reducing the formation of associated fibrocartilage.

(2) The functionality produced by the dense junction zone: this dense junction zone prevents synovial fluid from diffusing into the bone. This generates hydrostatic pressure within the cartilage layer—a critical factor for chondrogenesis. This improves hyaline cartilage formation.

(3) The tapered design: this allow the scaffold to be delivered to the osteochondral defect easily without "hard pushing" to prevent damage of the host tissue. The bone component of the scaffold "rests" on the surrounding bone tissue to form strong mechanical support to the overlying cartilage layers. At the same time, the scaffold can generate mechanical stimulation to the bone under dynamic loading.

Example 1: Nano-Hydroxyapatite Coating Improves Cell Growth on Titanium Matrix

Figure 6:
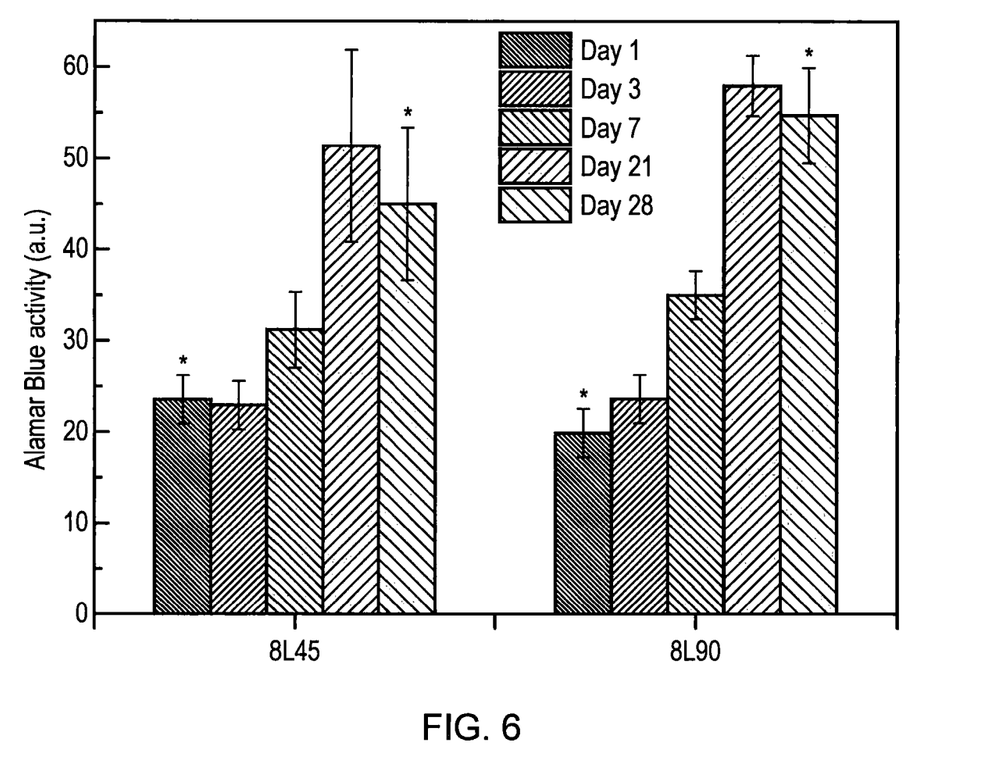
FIG. 6: Alamar blue activity of the sheep BMSCs in titanium scaffold.

Titanium scaffold is used for the bone section of the osteochondral scaffold. Sheep bone marrow derived stem cells were used for evaluation of the cellular performance. Examination revealed that the cells attached to the titanium surface and can proliferate in the titanium scaffold over the 28 days culture period, as demonstrated by Alamar blue analysis shown in FIG. 6.

Figure 7:
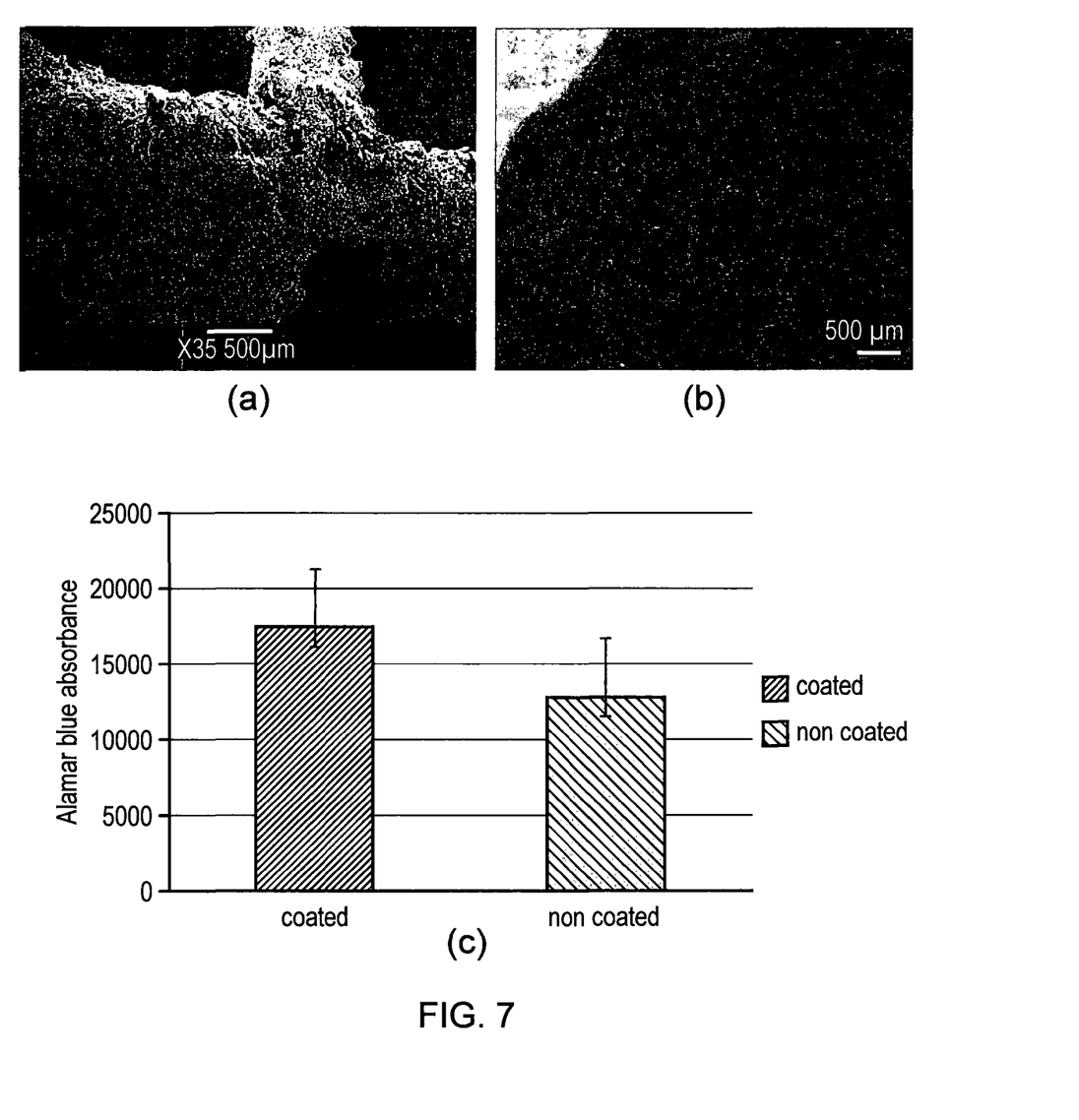

To improve the cells growth and bone formation within the titanium matrix, the titanium scaffold could be coated with a thin layer (1-10 micro meter) of nano-hydroxyapatite by electro-chemical deposition technique, as shown in FIG. 7a. The in vivo evaluation using sheep bone marrow derived stem cells indicated an increase in number of cells seeded on the scaffolds within 21 days, and presence of metabolically active and proliferating cells on both HA coated and non-coated samples, as shown in FIG. 7b Alamar blue analysis indicated that the cells on hydroxyapatite coated titanium have a higher proliferate rate than that of non-coated titanium scaffold (FIG. 7c).

Example 2. In Vitro Evaluation of the Osteochondral Scaffold

Figure 8:
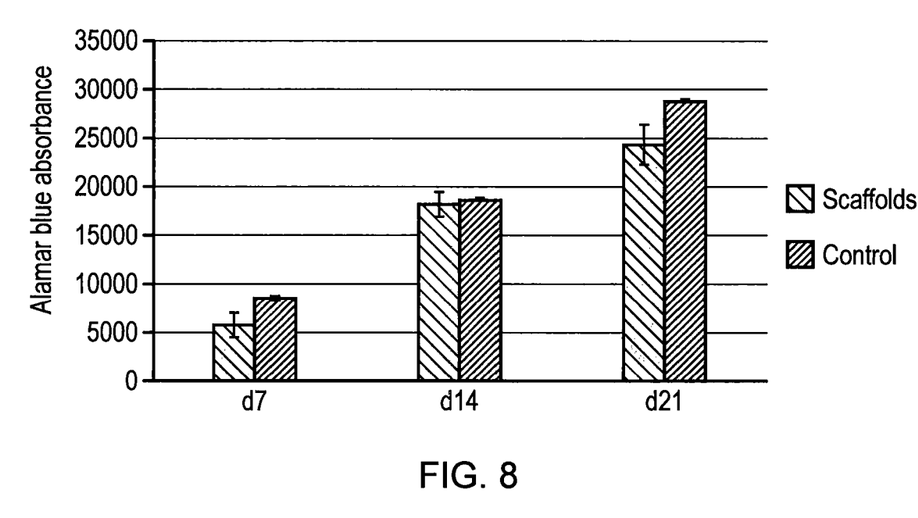
FIG. 8: Alamar blue activity of cells in the osteochondral scaffold of the invention and control scaffold.

Sheep bone marrow mesenchymal stem cells were used to evaluate the in vitro performance of the tri-layered osteochondral scaffold based on the titanium/PLGA/collagen system. Tri-layered collagen-hydroxyapatite osteochondral scaffold was used as control. The tissue culture was performed in static culture in normal culture medium. Alamar blue analysis indicated an increase in number of cells seeded on the scaffolds within 21 days (FIG. 8). The presence of metabolically active and proliferating cells on both the invented osteochondral scaffold and on the control scaffold were shown within 21 days culture. The titanium/PLGA/collagen osteochondral scaffold exhibited persistent higher Alamar blue activity than the control scaffold over 21 days' culture.

Example 3. The Osteochondral Scaffold Achieves Stable Mechanical Fixation

Figure 9:
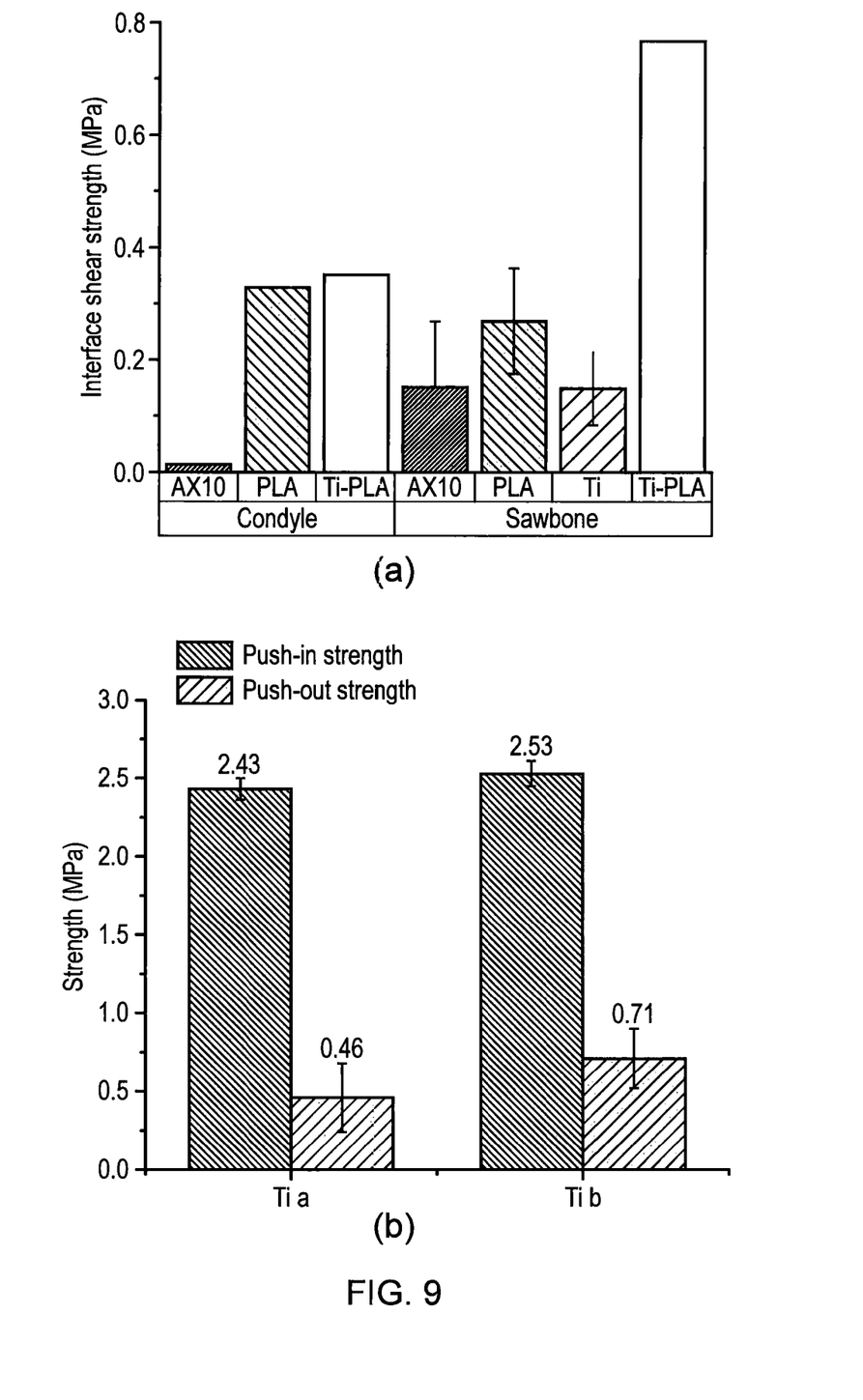

Sheep condyle and Sawbone were used to test the mechanical fixation of the scaffold. For this test, cylindrical osteochondral scaffold comprised of a lower titanium section and an upper PLA section. Multi-layered collagen-hydroxyapatite composite scaffolds were used as control. The mechanical fixation was determined in terms of interface shear strength and push-in and push-out strength. It was observed that both PLA and titanium-PLA scaffold have higher interface shear strength than the control scaffold in both sheep condyle and Sawbone model tests. In both cases, titanium-PLA double layers composite scaffold exhibited the higher interface shear strength, as shown in FIG. 9a.

The titanium scaffold was further evaluated in sheep chodyle model by push-in and push-out tests. It revealed that the push-in strength for a 10 mm diameter 10 mm thick cylindrical scaffold reached 2.43 MPa for titanium scaffold and 2.53 MPa for titanium alloy scaffold (FIG. 9b). It is worth noting that wet tri-layered collagen-hydroxyapatite scaffold fell out from the condyle hole without push, suggesting the control scaffold was too weak to reach a stable mechanical fixation.

Example 4. In Vivo Performance Evaluation—Sheep Medial Femoral Condyle Model

In vivo performance of the invented osteochondral scaffold (scaffold group) was carried out in a sheep stifle joint model. Collagen-hydroxyapatite tri-layered osteochondral scaffold was used as control (control group). The surgeries were performed with one defect site created per stifle joint on the medial femoral condyle. The scaffolds (10 mm diameter and 10 mm thick) were gently inserted into the defects created by a surgical drill bit. Five sheep were used in this study based on power analysis. Surgeries and analysis were carried out at week 12 to assess the surgical approach, scaffold fixation and early in vivo response.

Repair of Cartilage Defect In Vivo Sheep Condyle Model Study

Figure 10:
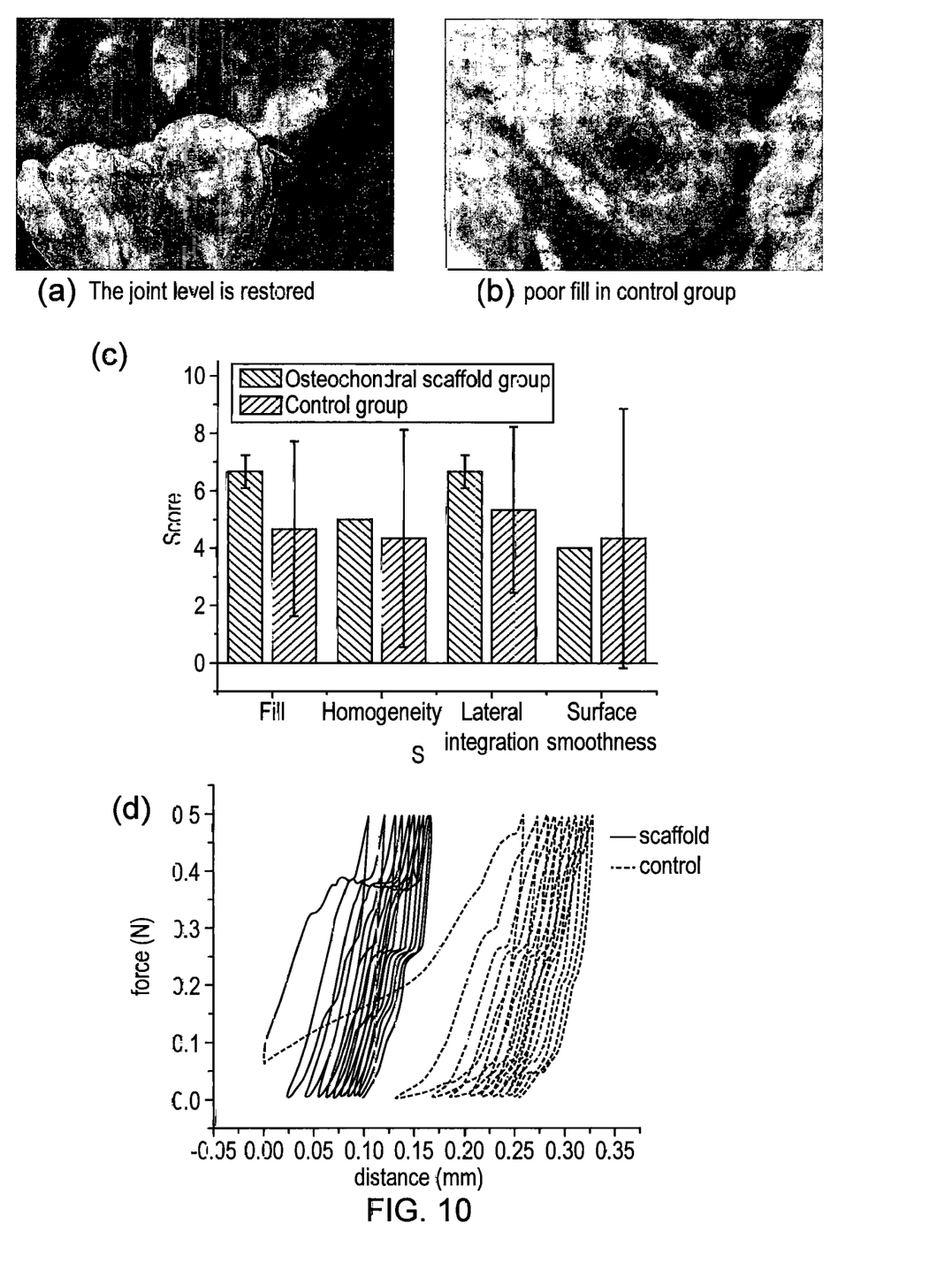

The specimens were retrieved three-month post operation. It was observed that the cartilage defect level was almost restored three month post operation in the scaffold group (FIG. 10a), while poor cartilage fill was revealed in the control group (FIG. 10b). The scores in the scaffold group with respect to cartilage fill, homogeneity, lateral integration and surface smoothness are higher than that of control group, as shown in FIG. 10c. Biomechanical property assessment by using a cyclic loading test demonstrated that the newly formed cartilage in the scaffold group exhibited resilient behaviour with a similar young's modulus to that of surrounding cartilage. In contrast, the cartilage in the control group exhibited more soft with much lower young's modulus, as shown in FIG. 10d.

pQCT examination revealed the new bone formed within the titanium matrix of the invented osteochondral scaffold and the scaffold integrated very well with the surrounding bone to form a strong mechanical fixation to support the overlying cartilage. The bone surrounding the scaffold has a mineral density above 700 g/cm$^3$, as determined by pQCT analysis; in contrast, poor bone fills were revealed in the control group, there are still large voids unfilled after 3 months. The bone surrounding the control scaffold has a much lower mineral density about 500 g/cm$^3$. This suggests that the control scaffold was unable to provide an appropriate mechanical support to the overlying cartilage. This may be the main reason leading to the poor cartilage fill and lower mechanical properties of the newly formed cartilage.

Example 5. Repair of Cartilage Defect—Clinical Dog Shoulder Model Study

A seven-month-old pet Italian Spinone dog (Flo) has naturally developed an osteochondral defect in her left humerus. The cartilage in Flo's left shoulder was severely degenerated and affects her subchondral bone. A tri-layer titanium/PLGA/collagen scaffold (10 mm diameter) was used to repair the osteochondral defect in Flo. Three month post-operation examination revealed that cartilage had regenerated well, newly formed cartilage integrated very well with the surrounding cartilage and matched the curvature of the joint perfectly. The dog's left shoulder had restored function, and the dog can run and jump normally. It has shown the scaffold has the strength needed to bear the physical load of the joints and its structure encourages consistent cartilage fill and a smooth articular surface.

The invention claimed is:

1. A multiphasic osteochondral scaffold for osteochondral defect repair, the scaffold comprising a bone phase and a cartilage phase, wherein the bone phase comprises a metallic support matrix and the cartilage phase comprises a polymeric matrix, and the scaffold comprises a non-porous layer between the bone phase and the cartilage phase, wherein the polymeric matrix partially overlaps with and is embedded in the support matrix, and wherein the non-porous layer is present in the region of overlap and acts to join the support matrix to the polymeric matrix, wherein, in use, the non-porous layer prevents synovial fluid from diffusing into the bone phase from the cartilage phase when subjected to dynamic compressive load, and wherein the non-porous layer is formed by at least partially melting one end of the polymeric matrix into the support matrix so that the melted polymeric matrix forms the non-porous layer in a portion of the support matrix.

2. The scaffold of claim 1, wherein the support matrix is formed of titanium.

3. The scaffold of claim 1, wherein the support matrix comprises one or more calcium phosphates.

4. The scaffold of claim 1, wherein the support matrix comprises collagen.

5. The scaffold of claim 1, wherein the support matrix is porous.

6. The scaffold of claim 5, wherein the unit cell size of the pores in the porous support matrix is between about 0.5 mm and about 2 mm.

7. The scaffold of claim 5, wherein the porous support matrix has a porosity of between about 30% and 70%.

8. The scaffold of claim 1, wherein the support matrix has a tapered profile so that the cross section of the support matrix at the lower end of the support matrix is less than the cross section of the support matrix at the upper end of the support matrix by the non-porous layer.

9. The scaffold of claim 1, wherein the support matrix has a tapered profile so that the dimensions of the support matrix at the lower end of the support matrix are less than the dimensions of the support matrix at the upper end of the support matrix.

10. The scaffold of claim 1, wherein the scaffold has a tapered profile so that the dimensions of the scaffold at the lower end are less than the dimensions of the scaffold at the upper end.

11. The scaffold of claim 9, wherein the support matrix or scaffold is tapered such that it is shaped as a truncated cone structure.

12. The scaffold of claim 9, wherein the angle of the taper is between about 5° and about 30°.

13. The scaffold of claim 1, wherein the polymeric matrix is formed of poly(lactic-co-glycolic acid) (PLGA), polylactic acid (PLA) or polycaprolactone (PCL).

14. The scaffold of claim 13, wherein the polymeric matrix further comprises collagen.

15. The scaffold of claim 1, wherein the polymeric matrix is porous.

16. The scaffold of claim 15, wherein the unit cell size of the pores in the polymeric matrix is between about 50 μm and about 300 μm.

17. The scaffold of claim 1, wherein the non-porous layer is formed from the same polymer as the polymeric matrix.

18. The scaffold of claim 1, wherein the non-porous layer is formed of poly(lactic-co-glycolic acid) (PLGA), polylactic acid (PLA) or polycaprolactone (PCL).

19. The multiphasic osteochondral scaffold of claim 1, the scaffold comprising a bone phase and a cartilage phase, wherein the bone phase comprises a porous support matrix and the cartilage phase comprises a porous polymeric matrix, and the scaffold comprises a non-porous layer between the bone phase and the cartilage phase, wherein the porous support matrix is formed of titanium and further comprises hydroxyapatite and collagen, wherein the porous polymeric matrix is formed of poly(lactic-co-glycolic acid) (PLGA), polylactic acid (PLA) or polycaprolactone (PCL) and further comprises collagen, and wherein the polymeric matrix partially overlaps with the support matrix and the non-porous layer is present in the region of overlap and is formed of the same polymer as the polymeric matrix.

20. The scaffold of claim 3, wherein the support matrix comprises beta-tricalcium phosphate, hydroxyapatite and/or biphasic calcium phosphate.

21. The scaffold of claim 1, wherein the non-porous layer has a thickness of between about 0.5 mm and about 2 mm.

\* \* \* \* \*